United States Patent
Kärcher et al.

(10) Patent No.: US 10,004,524 B2
(45) Date of Patent: Jun. 26, 2018

(54) INSTRUMENT FOR CARRYING OUT MEDICAL INTERVENTIONS

(71) Applicant: Karl Storz SE & Co. KG, Tuttlingen (DE)

(72) Inventors: Daniel Kärcher, Radolfzell (DE); Jochen Stefan, Wald (DE)

(73) Assignee: Karl Storz SE & Co. KG, Tuttlingen (DE)

( * ) Notice: Subject to any disclaimer, the term of this patent is extended or adjusted under 35 U.S.C. 154(b) by 383 days.

(21) Appl. No.: 14/627,906

(22) Filed: Feb. 20, 2015

(65) Prior Publication Data

US 2015/0238211 A1    Aug. 27, 2015

(30) Foreign Application Priority Data

Feb. 21, 2014    (DE) .......................... 10 2014 203 168

(51) Int. Cl.
*A61B 17/00* (2006.01)
*A61B 17/28* (2006.01)
(Continued)

(52) U.S. Cl.
CPC ........ *A61B 17/29* (2013.01); *A61B 17/00234* (2013.01); *A61B 17/2816* (2013.01); *A61B 2017/294* (2013.01); *A61B 2017/2927* (2013.01); *A61B 2017/2929* (2013.01); *A61B 2017/2939* (2013.01); *A61B 2017/2947* (2013.01); *A61B 2017/320044* (2013.01)

(58) Field of Classification Search
CPC .............. A61B 17/29; A61B 17/00234; A61B 17/2816; A61B 2017/2927; A61B 2017/2929; A61B 2017/2939; A61B 2017/294; A61B 2017/2947; A61B 2017/320044

See application file for complete search history.

(56) References Cited

U.S. PATENT DOCUMENTS 7,540,867 B2 *  6/2009  Jinno .................... A61B 34/71
                                                    414/7
7,942,895 B2 *  5/2011  Jinno .................... A61B 34/70
                                                    606/205
(Continued)

FOREIGN PATENT DOCUMENTS

DE      10314828 B3    7/2004
EP       2510888 A1   10/2012
(Continued)

*Primary Examiner* — Jing Ou
(74) *Attorney, Agent, or Firm* — Whitmyer IP Group LLC

(57) ABSTRACT

An instrument for carrying out medical interventions, including a tubular shaft running lengthwise along a shaft longitudinal axis, an instrument head, wherein the instrument head is supported on the tubular shaft in such a way as to be pivotable about an instrument head pivot axis, and at least part of the instrument head is rotatable about an instrument head longitudinal axis, and a wheel gear arrangement for moving the instrument head, wherein at least part of the instrument head can be driven by the wheel gear arrangement for the rotation about the instrument head longitudinal axis, and wherein the instrument head can be driven by the wheel gear arrangement for the pivoting about the instrument head pivot axis.

11 Claims, 3 Drawing Sheets

(51) Int. Cl.
   *A61B 17/29* (2006.01)
   *A61B 17/32* (2006.01)

(56) References Cited

U.S. PATENT DOCUMENTS

| | | | | |
|---|---|---|---|---|
| 2002/0040217 | A1* | 4/2002 | Jinno | B25J 3/04 606/1 |
| 2007/0023477 | A1* | 2/2007 | Whitman | A61B 17/07207 227/175.1 |
| 2008/0183193 | A1* | 7/2008 | Omori | A61B 17/29 606/130 |
| 2010/0191278 | A1* | 7/2010 | Lee | A61B 17/062 606/206 |
| 2010/0198253 | A1 | 8/2010 | Jinno et al. | |
| 2011/0106146 | A1* | 5/2011 | Jeong | A61B 17/29 606/208 |
| 2011/0152922 | A1* | 6/2011 | Jeong | A61B 17/29 606/205 |
| 2014/0246476 | A1* | 9/2014 | Hall | A61B 17/068 227/175.1 |

FOREIGN PATENT DOCUMENTS

| | | | |
|---|---|---|---|
| WO | 2013002063 | A1 | 1/2013 |
| WO | 2014134034 | A2 | 9/2014 |

* cited by examiner

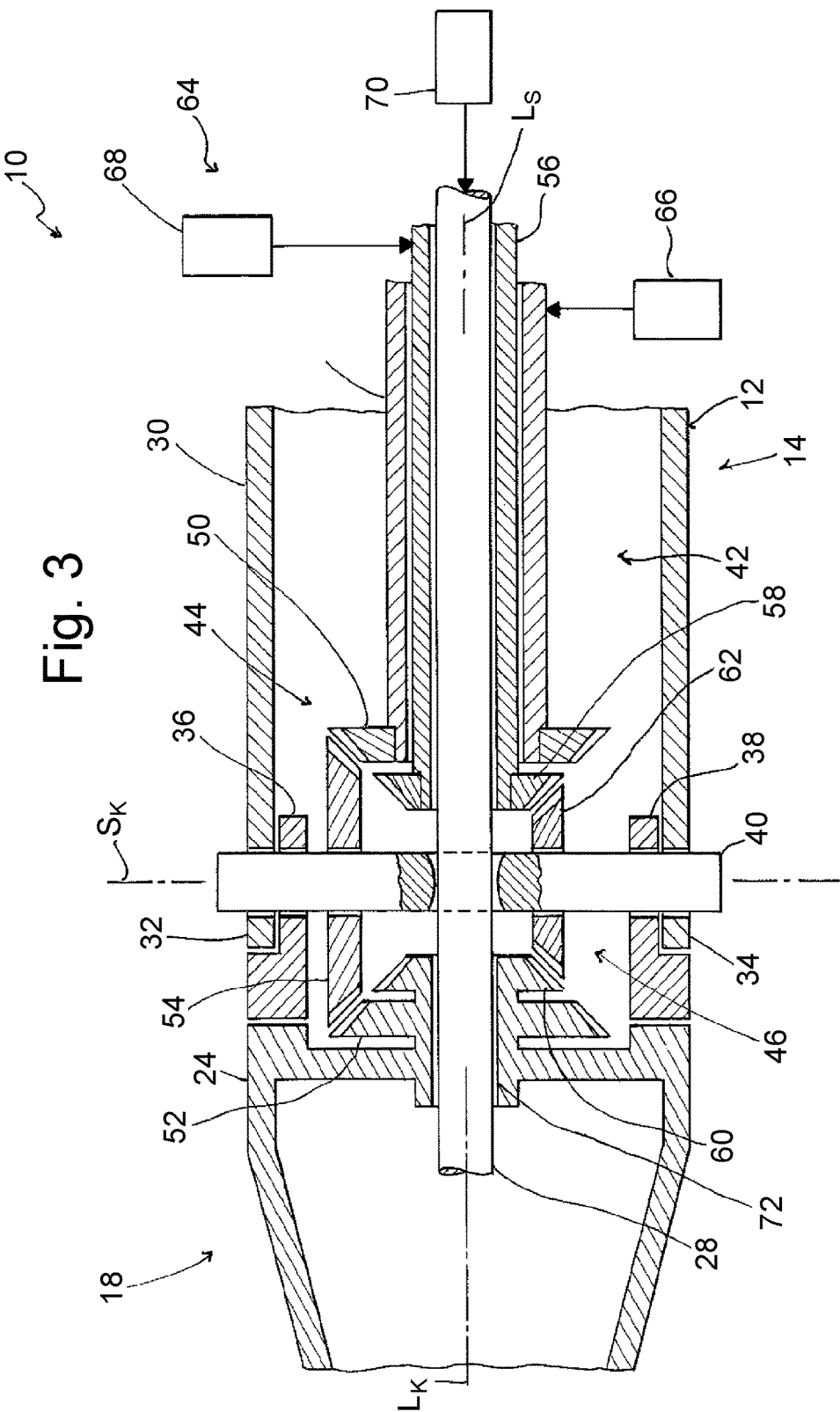

INSTRUMENT FOR CARRYING OUT MEDICAL INTERVENTIONS

FIELD OF THE INVENTION

The present invention relates to an instrument for carrying out medical interventions, comprising a tubular shaft running lengthwise along a shaft longitudinal axis, an instrument head, wherein the instrument head is supported on the tubular shaft in such a way as to be pivotable about an instrument head pivot axis, and at least part of the instrument head is rotatable about an instrument head longitudinal axis, and a wheel gear arrangement for moving the instrument head, wherein at least part of the instrument head can be driven by the wheel gear arrangement for the rotation about the instrument head longitudinal axis. Instruments of this kind, also known as tubular shaft instruments, are used, for example, in the context of endoscopic, minimally invasive surgical interventions, for the purpose of manipulating or separating tissue.

BACKGROUND OF THE INVENTION

DE 103 14 828 B3 discloses an instrument which is configured with a tubular shaft and in which an instrument head in the distal end area of the tubular shaft is connected pivotably to the latter. Part of the instrument head is rotatable about a rotation axis that is substantially orthogonal with respect to the axis of the pivot connection between the instrument head and the tubular shaft. In order to drive the rotation of this part of the instrument head, a wheel gear arrangement is provided which is designed as a bevel gear arrangement and which comprises an input shaft extending in the tubular shaft, with an input bevel gear supported in a rotationally fixed manner thereon, an output bevel gear for conjoint rotation with the rotatable part of the instrument head, and a transmission bevel gear meshing with these. With this bevel gear arrangement, the part of the instrument head supporting in particular the tools for a surgical intervention can be moved in rotation. In order to pivot the instrument head with respect to the tubular shaft, a pushing tube is arranged in the tubular shaft and is coupled, by way of a hinge connection, to the part of the instrument head articulated on the tubular shaft. By movement of the pushing tube in the interior of the tubular shaft, an actuating force is exerted on the instrument head, such that the latter pivots about a pivot axis with respect to the tubular shaft.

SUMMARY OF THE INVENTION

The object of the present invention is to make available an instrument for carrying out medical interventions which, while being of simple construction, permits precise actuation.

According to the invention, this object is achieved by an instrument for carrying out medical interventions, comprising a tubular shaft running lengthwise along a shaft longitudinal axis, an instrument head, wherein the instrument head is supported on the tubular shaft in such a way as to be pivotable about an instrument head pivot axis, and at least part of the instrument head is rotatable about an instrument head longitudinal axis, and a wheel gear arrangement for moving the instrument head, wherein at least part of the instrument head can be driven by the wheel gear arrangement for the rotation about the instrument head longitudinal axis.

Provision is further made that the instrument head can be driven by the wheel gear arrangement for the pivoting about the instrument head pivot axis.

Therefore, in the construction according to the invention, the instrument head is driven by the wheel gear arrangement both for the pivoting and also for the rotation, such that additional mechanisms, e.g. a thrust rod, are not needed to generate the pivoting movement.

To be able to bring about the two states of movement, it is proposed that the wheel gear arrangement comprises a first wheel gear train with a first driving wheel, a first transmission wheel and a first driven wheel, and a second wheel gear train with a second driving wheel, a second transmission wheel and a second driven wheel. Provision is then advantageously made that the first transmission wheel is in transmitting interaction with the first driving wheel and the first driven wheel, while the second transmission wheel is in transmitting interaction with the second driving wheel and the second driven wheel. Therefore, in the construction according to the invention, the wheel gear arrangement comprises two wheel gear trains which are basically constructed independently of each other but which interact in order to generate the different states of movement.

To easily allow the two wheel gear trains to act jointly on the instrument head, it is proposed that the first driven wheel and the second driven wheel are arranged concentrically with respect to the instrument head longitudinal axis and/or are connected for conjoint rotation with the part of the instrument head rotatable about the instrument head longitudinal axis.

On the drive side too, a construction that is easy to implement and of small overall size and that permits interaction of the two wheel gear trains can be obtained if the first driving wheel and the second driving wheel are arranged concentrically with respect to the shaft longitudinal axis and are rotatable about the shaft longitudinal axis. A very compact structure can be achieved in this way by virtue of the fact that the first driving wheel is rotationally fixed on a first input shaft, the second driving wheel is rotationally fixed on a second input shaft, and the first input shaft is designed as a hollow shaft receiving the second input shaft.

The first transmission wheel and the second transmission wheel can be arranged such that they are rotatable about a common transmission wheel rotation axis, which can advantageously correspond to the instrument head pivot axis. It is thereby ensured that, independently of the pivot position of the instrument head, the wheels on the input side and the wheels on the output side can always interact uniformly with the transmission wheels.

To be able, on the one hand, to easily connect the instrument head pivotably to the tubular shaft, and, on the other hand, also be able to achieve a defined positioning for the transmission wheels, it is proposed that at least one instrument head pivot pin is provided which connects the instrument head, pivotably about the instrument head pivot axis, to the tubular shaft, and that the first transmission wheel and the second transmission wheel are supported rotatably on at least one instrument head pivot pin.

The two states of movement discussed above, namely the rotation and pivoting of the instrument head or of at least part thereof by means of the wheel gear trains that interact but are basically drivable independently of each other, can be achieved in a particularly simple and advantageous manner if the first transmission wheel and the second transmission wheel are arranged lying opposite each other with respect to the instrument head longitudinal axis and/or the shaft longitudinal axis. In particular, this positioning also permits the parallel action of the two transmission wheels on the instrument head, so as to generate a pivot torque acting on the instrument head.

Particularly simple actuation of the two wheel gear trains, in order to obtain the interaction thereof for generating the two states of movement, can be achieved by virtue of the fact that the first wheel gear train and the second wheel gear train have the same speed conversion ratio, preferably 1:1. This makes it possible to drive the two driving wheels in the same direction or in opposite directions at the same speed, but at the same time also to achieve the same speed of two wheel gear trains on the output side.

Along with a simple construction, a reliable torque transmission interaction of the different wheels of the wheel gear arrangement can be ensured by virtue of the fact that the wheel gear arrangement is a bevel gear arrangement with a first bevel gear train and a second bevel gear train, wherein the first bevel gear train comprises a first input bevel gear, a first transmission bevel gear and a first output bevel gear, and the second bevel gear train comprises a second input bevel gear, a second transmission bevel gear and a second output bevel gear. In this case, provision can be made, for example, that the first transmission bevel gear is in transmitting interaction, preferably in meshing engagement, with the first input bevel gear on the one hand and the first output bevel gear on the other hand, while the second transmission bevel gear is in transmitting interaction, preferably in meshing engagement, with the second input bevel gear and the second output bevel gear.

To ensure that the instrument constructed according to the invention is able to be used in surgical interventions, for example for removing tissue samples, a jaw part can be supported on the instrument head in such a way as to be pivotable about a jaw part pivot axis. In order to actuate the jaw part, a pivot actuation rod can be provided, which extends through the instrument head and the tubular shaft and is preferably flexible. The flexibility of the pivot actuation rod ensures that the pivot actuation is independent of the pivot positioning of the instrument head with respect to the tubular shaft.

To guide the pivot actuation rod through the tubular shaft in particular, it is proposed that the second input shaft is designed as a hollow shaft receiving the pivot actuation rod. In this case, mutual interference with an instrument head pivot pin, which binds the instrument head to the tubular shaft, can be avoided by virtue of the fact that the instrument head pivot pin has a through-opening for the pivot actuation rod.

To actuate the instrument head, i.e. to attain the two states of movement of rotation and pivoting, it is further proposed that a drive arrangement is provided for driving the instrument head for the pivoting movement about the instrument head pivot axis and for the rotation movement about the instrument head longitudinal axis. This drive arrangement can in principle comprise one or more actuation members that are to be actuated manually, but it can also be in motor form, with one or more drive motors acting on the input-side bevel gears or on the shafts carrying the latter.

BRIEF DESCRIPTION OF THE DRAWINGS

The present invention is described in detail below with reference to the attached figures, in which:

FIG. 3 shows a schematic diagram of two bevel gear trains and their interaction with the instrument head.

DETAILED DESCRIPTION OF THE INVENTION

Figure 1:
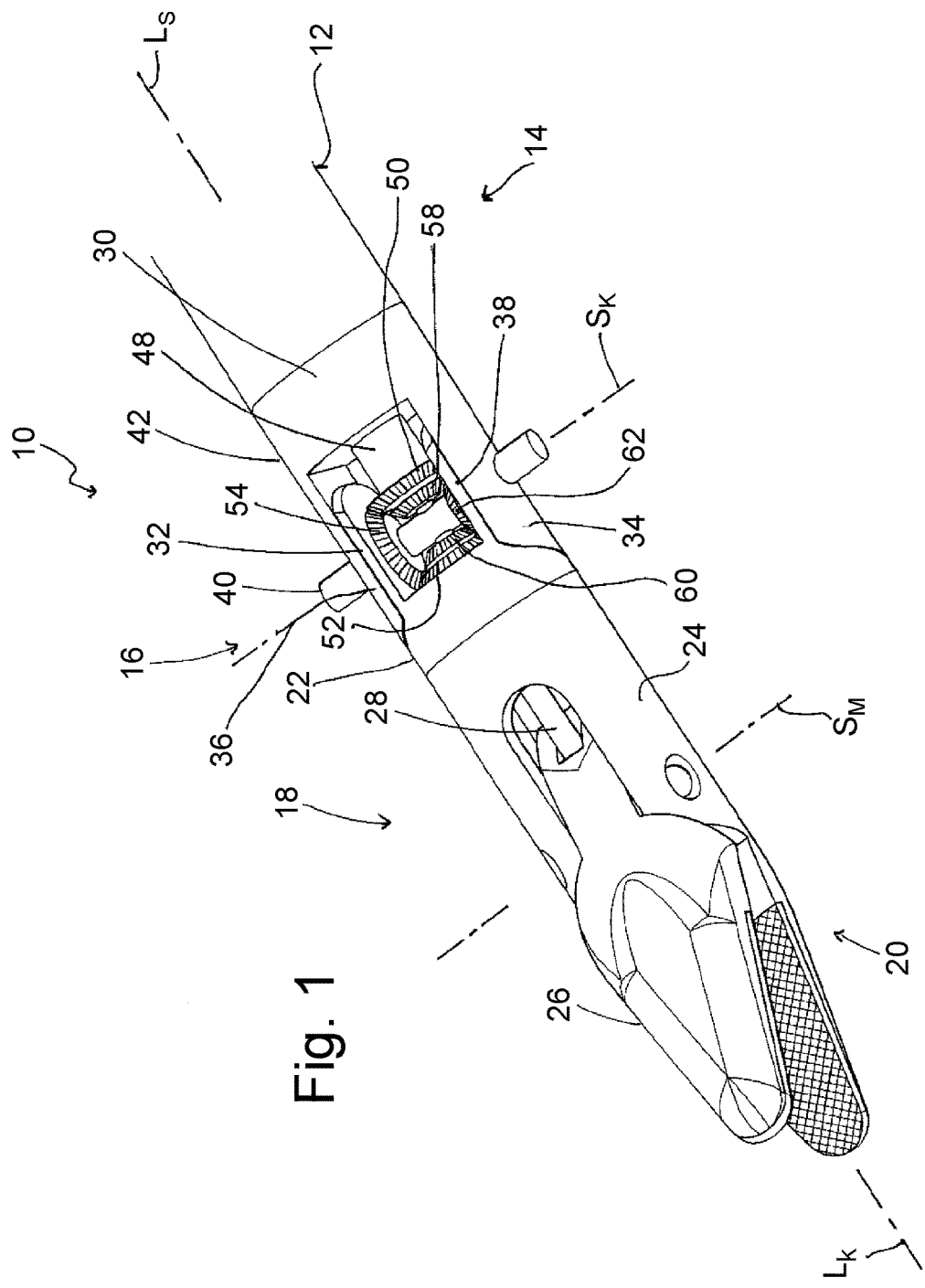
FIG. 1 shows a perspective view of part of an instrument for carrying out medical interventions, with two bevel gear trains.
Figure 2:
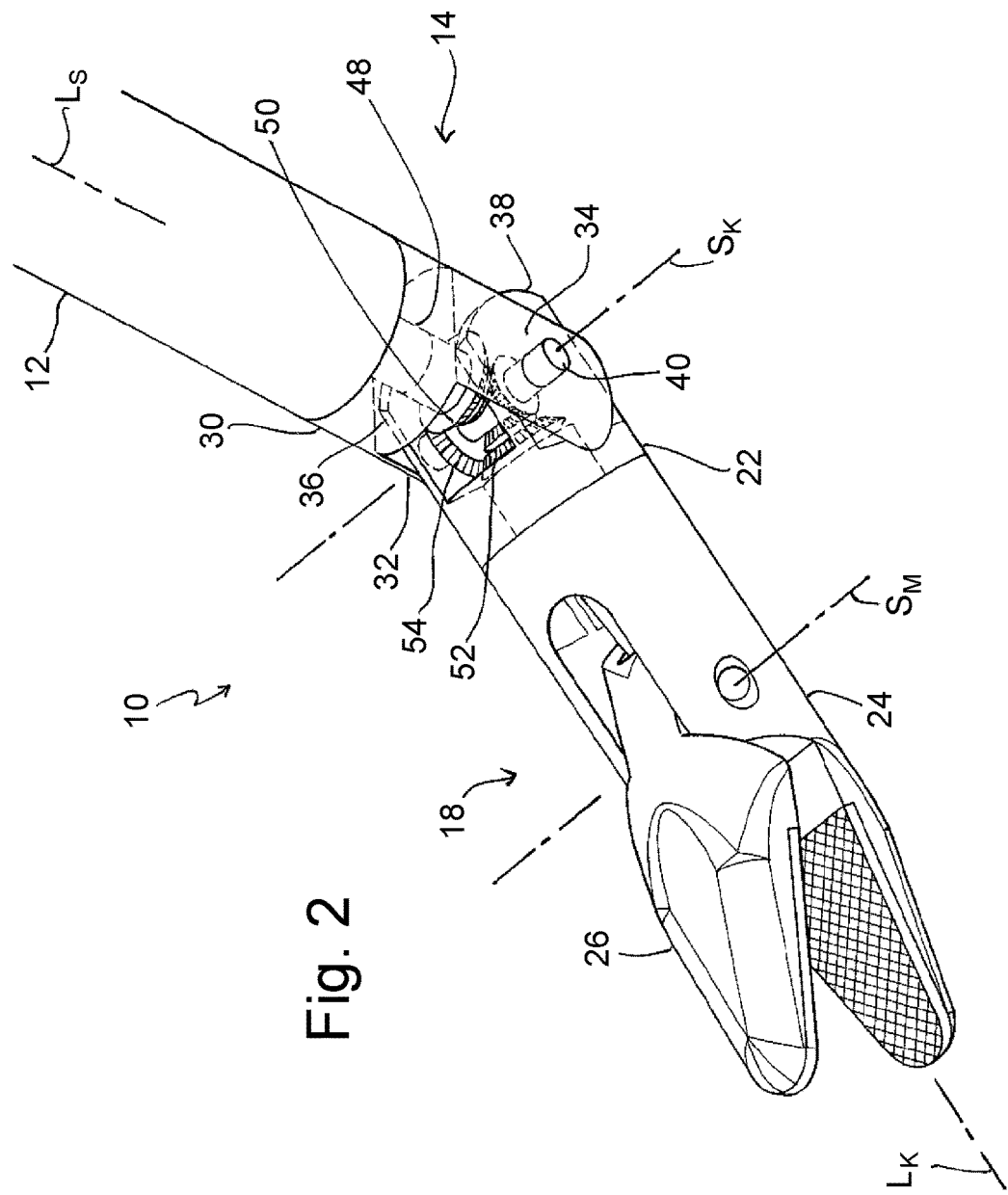
FIG. 2 shows the instrument from FIG. 1, with the instrument head pivoted with respect to a tubular shaft.

FIGS. 1 and 2 show an instrument that can be used to carry out endoscopic, minimally invasive medical interventions, for example for manipulating or removing tissue. The instrument, designated generally by 10, comprises an elongate tubular shaft 12, which can be in one or more parts and, in its distal end area 14, is connected to an instrument head 18 in a hinge area 16. The instrument head 18 forms in is entirety the distal end area 20 of the instrument 10. The instrument head 18 is constructed in several parts, with a first head part 22 which, in a manner described below, is connected to the tubular shaft 12 in an articulated manner in the hinge area 16. A second head part 24, adjoining the first head part 22, is pivotable together with the first head part 22 about an instrument head pivot axis $S_K$ with respect to the tubular shaft 12 and is rotatable with respect to the tubular shaft 12 and also with respect to the first head part 22 about an instrument head longitudinal axis $L_K$. A jaw part 26 is supported on the second head part 24 in such a way as to be pivotable about a jaw part pivot axis $S_M$. By pivoting the jaw part 26, the latter can be moved with respect to the second head part 24 so as to remove and/or release a tissue sample, for example. This pivoting movement of the jaw part 26 can be brought about by a pivot actuation rod 28 which is connected to the jaw part 26 for example in an articulated manner and which extends all the way through the instrument 10, i.e. the head part 18 and the tubular shaft 12.

In the hinge area 16, the tubular shaft 12, or a portion designed as the distal end part 30 thereof, has two articulated tabs 32, 34 which are arranged at a distance from each other transversely with respect to a shaft longitudinal axis $L_S$, e.g. longitudinal central axis. The instrument head 18, or the first head part 22 thereof, correspondingly has two articulated tabs 36, 38 which are arranged at a distance from each other transversely with respect to an instrument head longitudinal axis $L_K$, e.g. longitudinal central axis, but in such a way that they lie inside the two articulated tabs 32, 34 of the tubular shaft 12. An instrument head pivot pin 40 passes through mutually aligned openings that are provided in the articulated tabs 32, 34, 36, 38. For example, the instrument head pivot pin 40 can be firmly connected either to at least one of the articulated tabs 32, 34 or to at least one of the articulated tabs 36, 38, in order to prevent the instrument head pivot pin 40 from moving out of the openings that receive it. The component that is not firmly connected with any of its articulated tabs to the instrument head pivot pin 40 can execute a pivoting or rotating movement on the instrument head pivot pin 40 held securely with respect to the other component. It will be noted here that the instrument head pivot pin 40 does not necessarily have to protrude laterally beyond the outer articulated tabs 32, 34 to the extent shown. To avoid an obstruction to introducing the instrument 10 into a body, it is advantageous that the instrument head pivot pin 40 ends substantially flush with the outer surface of the tubular shaft 12 for example, i.e. does not protrude beyond said surface.

To bring about the pivoting of the instrument head 18 about the instrument head pivot axis $S_K$ and the rotation of the instrument head 18, or of the second head part 24, about the instrument head longitudinal axis $L_K$, the instrument 10 has a wheel gear arrangement designed as a bevel gear arrangement 42. The structure and the function of this bevel gear arrangement 42 for generating the two movements discussed above is described in detail below with reference to FIG. 3.

The bevel gear arrangement 42 comprises two bevel gear trains 44, 46 which interact in order to generate the two states of movement discussed above. The first bevel gear train 44 comprises a first input bevel gear 50 provided on a first input shaft 48. The first input shaft 48 advantageously extends coaxially with respect to the shaft longitudinal axis $L_S$ in the tubular shaft 12 and advantageously ends in the hinge area 16 in such a way that the first input bevel gear 50 provided thereon is arranged in the space left free by the articulated tabs 32, 34, 36, 38. It will be noted in this context that the shaft longitudinal axis $L_S$ can basically be defined by a rotation axis of the first input shaft 48 or of the first input bevel gear 50 or also of corresponding component groups of the second bevel gear train 46 explained below. It is advantageous, but not compulsory, if such a rotation axis coincides with a longitudinal central axis of the tubular shaft 12.

The first bevel gear train 44 moreover comprises a first output bevel gear 52. The latter is arranged for conjoint rotation with the second head part 24 and is arranged centrally with respect to the instrument head longitudinal axis $L_K$.

For torque transmission between the first input bevel gear 50 and the first output bevel gear 52, a first transmission bevel gear 54 of the first bevel gear train 44 is provided. The first transmission bevel gear 54 is supported rotatably on the instrument head pivot pin 40 and, for example by bearing on the articulated tab 36 on the one hand and on the two bevel gears 50, 52 on the other hand, is secured against displacement on the instrument head pivot pin 40. Of course, measures could also be provided directly on the instrument head pivot pin 40, for example in the form of steps, securing rings or the like, which prevent displacement of the first transmission bevel gear 54 along the instrument head pivot pin 40.

The second bevel gear train 46 comprises a second input shaft 56 extending in the tubular shaft 12. This second input shaft 56 extends inside the first input shaft 48 designed as a hollow shaft and, with the latter, is advantageously arranged substantially concentrically with respect to the shaft longitudinal axis $L_S$. In its end area protruding beyond the first input shaft 48, the second input shaft 56 has a second input bevel gear 58 arranged for conjoint rotation therewith.

On the instrument head 18, or on the second head part 24 thereof, a second output bevel gear 60 is provided which is associated with the second input bevel gear 58 and is arranged centrally with respect to the instrument head longitudinal axis $L_K$. This second output bevel gear 60 is therefore arranged, together with the first output bevel gear 52, concentrically with respect to the instrument head longitudinal axis $L_K$ and, in addition, is firmly connected to the first output bevel gear 52 and also the second head part 24 for conjoint rotation about the instrument head longitudinal axis $L_K$. This firm connection can be achieved by designing the two output bevel gears 52, 60 and the second head part 24 as separate components and subsequently firmly connecting them. Alternatively, at least two of these components could be produced integrally with each other. Moreover, the two output bevel gears 52, 60 could be provided by different cone portions of a common output bevel gear.

The second bevel gear train 46 furthermore comprises a second transmission bevel gear 62. The latter is supported rotatably on the instrument head pivot pin 40. The second transmission bevel gear 62 transmits a torque between the second input bevel gear 58 and the second output bevel gear 60. In association with the second transmission bevel gear 62, suitable measures can be provided on the instrument head pivot pin 40 in order to prevent a displacement of the second transmission bevel gear 62 on the instrument head pivot pin 40.

To be able to pivot and turn the instrument head via the two bevel gear trains 44, 46 of the bevel gear arrangement 48, a drive arrangement is provided, generally designated here by 64. On the proximal end area (not shown) of the tubular shaft 12 or of an assembly coupled to the latter, this drive arrangement can, for example, have a drive unit 66, 68 associated with each input shaft 48, 56. For example, these drive units 66, 68 can be configured as motors, that is to say can each comprise, for example, an electric drive motor or the like, although they can also equally well comprise a single drive motor that is able to act on both input shafts 48, 56 via a gear mechanism. A manual actuation member in association with each of the input shafts 48, 56 or both input shafts can also be used for the actuation.

The actuation of the jaw part 26 via the pivot actuation rod 28 can be effected by a drive unit 70 acting on the pivot actuation rod 28 at the proximal end area of the tubular shaft 12, for example. This can also be in motor form or can be designed for manual actuation by a physician using the instrument 10. To be able to guide the pivot actuation rod 28 from the instrument head 18 into the area of the tubular shaft 12, a through-opening 72 is formed in the second head part 24, advantageously concentrically with respect to the instrument head longitudinal axis $L_K$, through which opening the pivot actuation rod 28 is guided from the instrument head 18. A corresponding through-opening 74 is also provided in the instrument head pivot pin 40. In order to prevent jamming or wedging of the pivot actuation rod 28 in the through-opening 74 during the actuation of the jaw part 26, this through-opening 74 can be designed widening towards its two end areas. The pivot actuation rod 28 then extends further through the second input shaft 56 likewise designed as a hollow shaft, e.g. substantially coaxially with respect to the shaft longitudinal axis $L_S$, as far as the proximal end area of the tubular shaft 12. To permit the pivoting of the instrument head 18 about the instrument head pivot axis $S_A$, i.e. not impede it by the pivot actuation rod 28, the latter is flexible, such that it is able to bend, particularly in the area where it passes through the through-opening 74, and, in this bent state, can also be moved through the through-opening 74 upon activation of the drive unit 70. For this purpose, for example, a thin wire, preferably a steel wire, or also a corresponding plastic element, can be provided as pivot actuation rod 28, or as the portion thereof guided in the area of the hinge 16.

Before the function of the bevel gear arrangement 42 for the pivoting and rotating of the instrument head 18 is described below, also with reference to FIG. 3, it will be noted that the above-discussed bevel gears 50, 52, 54 of the first bevel gear train 44 and also the bevel gears 58, 60, 62 of the second bevel gear train 46 for the reliable torque transmission are advantageously designed as toothed wheels which are in meshing engagement with one another. The design and size of the intermeshing teeth of the first bevel gear train 44, on the one hand, and of the second bevel gear train 46, on the other hand, are in principle independent of each other in this case. The design of the wheel gear arrangement with toothed wheels, the latter being designed in particular as bevel gears, is particularly advantageous, on the one had because of the compact structure that can thus be obtained, and, on the other hand, because of the precise mobility of the head part 24, ensured by the meshing engagement of the different teeth of the wheels or bevel gears. However, it will be noted that the wheel gear arrangement can be designed with other wheels that can be used for torque transmission. For example, frictional wheels, which can also be designed as bevel gears for example, can be used in one or both gear trains. The different gear trains can also be configured with contrate wheels or other types of wheels that can be made to interact for torque transmission, wherein the two gear trains can in particular also be designed differently in terms of the wheels provided for each of them.

In order to bring about a rotation of the instrument head 18, i.e. of the head part 24 thereof, using the bevel gear arrangement 42, the two input shafts 48, 56 are driven by the drive arrangement 64 for rotation in the same direction of rotation, advantageously also at the same speed. In view of the fact that the two transmission gear wheels 54, 62 lie opposite each other with respect to the shaft longitudinal axis $L_S$ and also the instrument head longitudinal axis $L_K$, i.e. are arranged on different sides of these axes, this rotation of the two input shafts 48, 56 in the same direction, and therefore also of the input bevel gears 50, 58 connected respectively thereto, also causes the two transmission gear wheels 54, 62 to rotate in different directions to each other about the instrument head pivot axis $S_K$, which as it were defines the rotation axis of these two transmission bevel gears 54, 62. A mutually different direction of rotation of the two transmission wheels 54, 62 has the effect that, because of their interaction with the output bevel gears 52, 60 on opposite sides with respect to the instrument head longitudinal axis $L_K$, these two output bevel gears 52, 60 are driven in rotation in the same direction of rotation about the instrument head longitudinal axis $L_K$. This means that the two driving torques transmitted by the bevel gear trains 44, 46 and introduced into the instrument head 18 add to each other, and, in this way, the second head part 24 is driven in rotation about the instrument head longitudinal axis $L_K$ with respect to the first head part 22.

To ensure that this parallel action of the two bevel gear trains 44, 46 does not cause jamming or to prevent these bevel gear trains 44, 46 from at least partially working against each other, it is important that the two bevel gear trains 44, 46 work with the same speed conversion ratio, assuming that the two input shafts 48, 56 are intended to be driven at the same speed. With input bevel gears 50, 58 that rotate at the same speed, it is only in this way possible to ensure that the two output bevel gears 52, 60, which are in principle connected to each other for conjoint rotation, are also driven in rotation at the same speed about the instrument head longitudinal axis $L_K$. An identical speed conversion ratio of the two bevel gear trains 44, 46 can be obtained, for example, if the mutually associated input and output bevel gears 50, 52 and 58, 60, respectively, generate identical conversion ratios, that is to say, for example, also provide identical diameter ratios. In the example shown, the diameter ratio and therefore the conversion ratio between input bevel gear 50 and output bevel gear 52 is 1:1 in the first bevel gear train 44. The same also applies to the input bevel gear 58 and the output bevel gear 60 of the second bevel gear train 46. This means that, in the example shown, the rotation movement of the two input shafts 48, 56 is transmitted 1:1 to the instrument head 18 or the second head part 24 thereof. For example, if the speed is to be reduced in order to achieve a more sensitive rotation of the second head part 24, this could be done, for example, by designing the two output bevel gears 52, 60 with a greater diameter than the associated input bevel gears 50, 58. However, this would also require a correspondingly staged configuration of the transmission gear wheels 54, with a first transmission gear wheel stage for interaction with the respective input bevel gear, and a second transmission gear wheel stage for interaction with the associated output bevel gear.

In order to generate a pivoting of the instrument head 18 about the instrument head pivot axis $S_K$ using the bevel gear arrangement 42, the two input shafts 48, 56 are driven by the drive arrangement 64, advantageously at the same speed, for rotation in opposite directions. Such a rotation of the two input shafts 48, 56 in opposite directions, and of the input bevel gears 50, 58 provided thereon, has the effect that the transmission bevel gears 54, 62 rotate relative to each other in the same direction about the instrument head pivot axis $S_K$. A rotation of the two transmission bevel gears 54, 62 in the same direction has the effect that the two output bevel gears 58, 60 connected for conjoint rotation with each other are driven in rotation in opposite directions. Since this is in principle not possible, because of these two output bevel gears 52, 60 being connected to each other for conjoint rotation, a torque about the instrument head pivot axis $S_K$ is exerted on the instrument head 18 by the transmission gear wheels 54, 62, such that the instrument head 18 pivots when the two input shafts 48, 56 are rotated in opposite directions about the instrument head pivot axis $S_K$. For example, starting from the state shown in FIG. 1, in which the instrument 10 is not angled and, for example, the shaft longitudinal axis $L_S$ and the instrument head longitudinal axis $L_K$ lie coaxially to each other, it is possible, with suitable driving of the two input shafts 48, 56, to achieve a pivoting movement to the state shown in FIG. 2, in which the instrument head 18 is angled with respect to the tubular shaft 12, at an angle different than 180°, and the instrument head longitudinal axis $L_K$ is also angled to a corresponding extent with respect to the shaft longitudinal axis $L_S$. In this state, these two axes $L_K$ and $L_S$ intersect each other, e.g. in the instrument head pivot axis $S_K$.

On account of the already discussed flexibility of the pivot actuation rod 28 for the jaw part 26, at least in the hinge area 16, a pivoting actuation of the jaw part 26 for removing or also for releasing tissue samples or the like is also possible in this state of the instrument head 18 pivoted with respect to the tubular shaft 12.

With the above-described structure of the bevel gear arrangement 42 with its two bevel gear trains 44, 46 interacting both for the pivoting and also for the rotation of the head part 18, a precise mobility of the instrument head 18 is ensured along with a compact and easy to implement design. The interaction of the two bevel gear trains 44, 46 also ensures that the two different movements of the instrument head 18, i.e. the rotation thereof, on the one hand, and the pivoting, on the other hand, do not influence each other. When a rotation movement is performed by suitable driving of the two input shafts 48, 56 at a suitable speed and direction of rotation, no pivoting is generated. Likewise, when a pivoting movement is performed by driving the two input shafts 48, 56 at a suitable speed and direction of rotation, no rotation movement is generated. The interaction of the two bevel gear trains 44, 46 with in each case the same speed conversion ratio is particularly advantageous since, in this case, the two input shafts 48, 56 can be driven at the same speed and in the same direction or different directions, for example via a common drive or a common actuation member, if appropriate with an interposed gear system. The interaction of the two bevel gear trains 44, 46 for the rotation and pivoting of the instrument head 18 could of course also be used if these have different speed conversion ratios from each other. In this case, however, it is advantageous to drive the two input shafts 48, 56 at a different speed, corresponding to this difference in the speed conversion ratio. This can be achieved in a particularly simple way if these two input shafts 48, 56 are assigned independently activatable drive units, for example electric motor drive units.

It will furthermore be noted that the structure according to the invention can of course also be used on instruments that have different uses or have a different basic design. Thus, the instrument head 18 could of course be of a different size, for example longer than is shown in the figures. The basic design or basic function of the present invention is also independent of the specific structural configuration or dimensioning of the tubular shaft receiving the two input shafts of the bevel gear trains and of the connection thereof to the respective drive units.

The invention claimed is:

1. An instrument for carrying out medical interventions, comprising:
    a tubular shaft running lengthwise along a shaft longitudinal axis;
    an instrument head supported on the tubular shaft in such a way as to be pivotable about an instrument head pivot axis which extends transversely with respect to an instrument head longitudinal axis, at least part of the instrument head being rotatable about the instrument head longitudinal axis; and
    a wheel gear arrangement for moving the instrument head;
    wherein at least part of the instrument head is configured to be driven by the wheel gear arrangement for rotation about the instrument head longitudinal axis;
    wherein the instrument head is configured to be driven by the wheel gear arrangement for the pivoting about the instrument head pivot axis;
    wherein the wheel gear arrangement comprises
        a first wheel gear train with a first driving wheel, a first transmission wheel rotatable about the instrument head pivot axis, and a first driven wheel, and
        a second wheel gear train with a second driving wheel, a second transmission wheel rotatable about the instrument head pivot axis, and a second driven wheel; and
    wherein the first driven wheel and the second driven wheel are arranged concentrically with respect to the instrument head longitudinal axis and are firmly connected for conjoined rotation with the part of the instrument head rotatable about the instrument head longitudinal axis.

2. The instrument according to claim 1, wherein the first driving wheel and the second driving wheel are arranged concentrically with respect to the shaft longitudinal axis and are rotatable about the shaft longitudinal axis.

3. The instrument according to claim 1, wherein the first driving wheel is rotationally fixed on a first input shaft, in that the second driving wheel is rotationally fixed on a second input shaft, and in that the first input shaft is designed as a hollow shaft receiving the second input shaft.

4. The instrument according to claim 3, wherein the second input shaft is designed as a hollow shaft receiving a pivot actuation rod.

5. The instrument according to claim 1, wherein at least one instrument head pivot pin is provided connecting the instrument head to the tubular shaft, such that the instrument head is pivotable about the instrument head pivot axis, and wherein the first transmission wheel and the second transmission wheel are supported rotatably on the at least one instrument head pivot pin.

6. The instrument according to claim 5, wherein an instrument head pivot pin has a through-opening for a pivot actuation rod.

7. The instrument according to claim 1, wherein the first transmission wheel and the second transmission wheel are arranged lying opposite each other with respect to the instrument head longitudinal axis and/or the shaft longitudinal axis.

8. The instrument according to claim 1, wherein the first wheel gear train and the second wheel gear train have the same speed conversion ratio, preferably 1:1.

9. The instrument according to claim 1, wherein the wheel gear arrangement is a bevel gear arrangement with a first bevel gear train and a second bevel gear train, wherein the first bevel gear train comprises a first input bevel gear, a first transmission bevel gear and a first output bevel gear, and the second bevel gear train comprises a second input bevel gear, a second transmission bevel gear and a second output bevel gear.

10. The instrument according to claim 1, wherein a jaw part is supported on the instrument head in such a way as to be pivotable about a jaw part pivot axis, and in that a pivot actuation rod, which extends through the instrument head and the tubular shaft and is preferably flexible, is assigned to the jaw part.

11. The instrument according to claim 1, wherein a drive arrangement is provided for driving the instrument head for pivoting movement about the instrument head pivot axis and for rotation movement about the instrument head longitudinal axis.

* * * * *